*(12)* United States Patent
Ishikawa et al.

(10) Patent No.: US 6,569,078 B2
(45) Date of Patent: May 27, 2003

(54) COIL APPARATUS FOR URINARY INCONTINENCE TREATMENT

(75) Inventors: Norio Ishikawa, Tokyo (JP); Shin Suda, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/770,205

(22) Filed: Jan. 29, 2001

(65) Prior Publication Data

US 2001/0011152 A1 Aug. 2, 2001

(30) Foreign Application Priority Data

Jan. 27, 2000 (JP) ........................................ 2000-018545

(51) Int. Cl.⁷ .............................................. A61B 17/52
(52) U.S. Cl. ............................................. 600/9; 600/13
(58) Field of Search ................................ 600/9, 29, 13

(56) References Cited

U.S. PATENT DOCUMENTS

| | | | | | |
|---|---|---|---|---|---|
| 3,554,184 | A | * | 1/1971 | Henry | 128/346 |
| 4,504,813 | A | * | 3/1985 | Strang | 336/216 |
| 4,937,546 | A | * | 6/1990 | Horng | 336/65 |
| 5,005,097 | A | * | 4/1991 | Matsuoka | 360/121 |
| 5,041,077 | A | * | 8/1991 | Kulick | 600/29 |
| 5,428,888 | A | * | 7/1995 | Hernandez-Ros et al. | 29/605 |
| 5,725,471 | A | | 3/1998 | Davey et al. | 600/13 |
| 5,833,595 | A | * | 11/1998 | Lin | 600/29 |
| 5,984,854 | A | | 11/1999 | Ishikawa et al. | 600/9 |
| 6,048,306 | A | * | 4/2000 | Spielberg | 600/29 |
| 6,086,525 | A | | 7/2000 | Davey et al. | 600/13 |
| 6,171,231 | B1 | * | 1/2001 | Connolly | 600/29 |
| 6,179,769 | B1 | * | 1/2001 | Ishikawa et al. | 600/9 |
| 6,223,750 | B1 | * | 5/2001 | Ishikawa et al. | 128/885 |
| 2001/0031906 | A1 | * | 10/2001 | Ishikawa et al. | 600/13 |

FOREIGN PATENT DOCUMENTS

| | | | | |
|---|---|---|---|---|
| GB | 1120131 A2 | * | 8/2001 | A61N/2/02 |
| JP | 9-276418 | | 10/1997 | A61N/1/40 |
| JP | 10-234870 | | 9/1998 | A61N/2/00 |

* cited by examiner

*Primary Examiner*—David A. Scherbel
*Assistant Examiner*—F. Nicloas
(74) *Attorney, Agent, or Firm*—Sughrue Mion, PLLC

(57) ABSTRACT

A core (5) is composed of a J-shaped front core portion (1), a J-shaped rear core portion (2), a U-shaped left core portion (3), and a U-shaped right core portion (4). These core portions (1 to 4) have one-side end portions which are substantially directed in one and the same direction and which are fixed to one another to thereby form a center portion (6). A coil (7) is wound on the center portion (6). The core (5) is attached to a core support member attached closely to a patient. In use, the coil apparatus is made close or near to the patient. When the coil (7) is supplied with a pulse current, pulse-like magnetic flux is generated in the purdendal nerve and pelvic floor muscle group of the patient so that an eddy current is induced. The patient in the region where magnetic flux is generated and an eddy current is generated, is stimulated sufficiently, so that urinary incontinence treatment is performed.

3 Claims, 6 Drawing Sheets

COIL APPARATUS FOR URINARY INCONTINENCE TREATMENT

BACKGROUND OF INVENTION

1. Field of Invention

The present invention relates to a coil apparatus for medically treating a urinary incontinence patient by generating magnetic flux to thereby induce an eddy current in the body of the patient when a coil apparatus is supplied with a pulse current.

2. Related Art

There is proposed an apparatus for medically treating a urinary incontinence patient by stimulating the pelvic floor muscle group, the purdendal nerve, or the like, of the patient with an eddy current induced by magnetic flux generated from a coil and given to the patient (JP-A-9-276418, JP-A-10-234870), in place of a well-known electric stimulation apparatus for medically treating a urinary incontinence patient by attaching stimulation electrodes and giving an electric pulse to the patient.

The proposed apparatus has made it possible to medically treat a urinary incontinence patient, noninvasively, with his or her clothes on, without pain and shock to the patient. Moreover, the proposed apparatus has made it possible to reduce electric power consumption.

Urinary incontinence is roughly classified into stress incontinence and urge incontinence. For giving medical treatment for stress incontinence, it is necessary to stimulate the pelvic floor muscle group of the patient and reinforce the weakened muscular system, such as the weakened pelvic floor muscle group, the weakened urethral sphincter group, or the like, of the patient to thereby strengthen the urethra-tightening force. On the other hand, for giving medical treatment for urge incontinence, it is necessary to stimulate the purdendal nerve and branches thereof derived from the second, third and fourth sacral nerves to thereby suppress the reflexive involuntary contraction of the bladder.

In order to perform such medical treatment by use of magnetic force, it is therefore important that the magnetic flux can reach the pelvic floor muscle group or the purdendal nerve and branches thereof efficiently.

In the coil apparatus, there are two kinds of coils for generating magnetic flux. One is an air-core coil, and the other is a cored coil. The air-core coil has two features as follows.

(1) It is easy to generate an intensive magnetic field because the magnetic field can be intensified in proportion to the intensity of the current.

(2) Magnetic lines of flux diverge from the center of the coil, so that magnetic flux reaches a wide region.

Accordingly, the air-core coil is advantageous in the case where the region to be stimulated is extended to a wide range. The air-core coil is, however, unsuitable for stimulation of a certain limited region. That is, the air-core coil has a disadvantage in that a wider region than intended is stimulated, and a large amount of electric power is consumed.

On the other hand, the cored coil has a feature that magnetic lines of flux can be concentrated in the core to thereby effectively stimulate a specific region. Hence, the cored coil has an advantage in that electric power consumed by the cored coil is very little in comparison with the air-core coil if the region to be stimulated is limited to a specific region. Therefore, a W-shaped core composed of two U-shaped core elements is heretofore used so that a considerably wide region can be stimulated, though, with the cored coil used. FIG. 12 shows the configuration of the W-shaped core. As shown in FIG. 12, the two U-shaped core elements 20 and 21 have one-side end portions fixed to each other at a fixation portion. The coil 22 is wound on the fixation portion of the core. This coil apparatus is used so that the core elements 20 and 21 are directed in a direction of the front-to-behind of the patient.

In such a coil apparatus, however, magnetic lines of flux are flattened (horizontally) in the direction of the front-to-behind of the patient so as to pass through the region of the patient to be stimulated. Hence, the coil apparatus has a disadvantage in that it does not stimulate all over the pelvic floor muscle group or the purdendal nerve.

Namely, as shown in FIG. 13($a$), the pelvic floor muscle group, which is located below a bone marrow, supports a bladder, a vagina, a uterus, a rectum or the like and is defined by levator consisting of a coccygeus muscle, an iliococcygeus muscle, pubococcygeus muscle or the like and a puborectal fillet (sling) surrounding the lower part of the rectum. The pelvic floor muscle group spreads in a horizontal direction. Further, second to fourth sacral nerves 101 are located in vicinity of the bladder as shown in FIGS. 13($a$) and ($b$). That is, the second to fourth sacral nerves serve as a trunk branching to the purdendal nerve controlling an external urethral sphincter 102 contracting the urethra. As viewed from the bottom of a buttocks, the second to fourth sacral nerves are innervated in right and left directions (FIG. 13($b$) only shows in right side. Left side thereof is omitted). Further, the pelvic nerve for contracting the sphincter muscle of the urinary bladder during urination is branched from the second to fourth sacral nerves.

Namely, the inventors find that it is necessary to sufficiently apply the magnetic flux to not only front-to-behind direction of the patient but also right-to-left direction thereof in consideration of width of the pelvic floor muscle group and right-to-left direction of the second to fourth sacral nerves and the purdendal nerve branched from the sacral nerves.

SUMMARY OF INVENTION

The present invention has been achieved in consideration of the disadvantages in the background art, and an object of the present invention is to provide a coil apparatus for urinary incontinence treatment, in which: electric power consumption can be reduced; and the region to be stimulated can be stimulated while the regions not to be stimulated are hardly stimulated.

The coil apparatus for urinary incontinence treatment according to the present invention comprises: a core including at least four U- or J-shaped core elements, the four core elements having one-side end portions and counter-side end portions opposite to the one-side end portions respectively, the one-side end portions being directed substantially in one and the same direction, the one-side end portions being fixed to one another at a portion which is defined as a center portion of the core, the counter-side end portions being extended in each direction respectively from the center portion where the one-side end portions are fixed to one another; a coil wound on the core; and a core support member to which the core is attached, the core support member being able to be disposed close or near to a patient.

In the aforementioned configuration, magnetic flux is generated between the fixation portion at which the core elements are fixed to one another and each of the counter-side end portions of at least the four core elements. The magnetic flux reaches all the specific region in the patient's body but the magnetic flux hardly reaches the other region. Hence, an eddy current is induced in the specific region so that urinary incontinence treatment is performed.

The core in the aforementioned configuration may be replaced by an integrally molded core having substantially the same whole shape of the first-mentioned core.

According to another aspect of the present invention, there can be provided a coil apparatus comprising a core, a coil and a core support member. The core includes a bowl-shaped or closed-end-tube-shaped base portion and a protrudent portion protruded from an inner center of the base portion. The coil is wound on the protrudent portion of the core. The core support member is attached close or near to a patient in a state in which the core is attached to the core support member.

Thus, magnetic flux is generated between the protrudent portion of the core and the edge portion of the base portion of the core. The magnetic flux reaches all over the specific region of the patient's body but hardly reaches the other region. An eddy current is induced in the specific region to perform urinary incontinence treatment.

According to the present invention, the magnetic flux generated from the core applied for a patient to at least forward to behind direction of the pelvic floor muscle group and right to left direction where the second to fourth sacral nerves innervated in said right to left direction or the purdendal nerve branched from the second to fourth sacral nerves.

DETAILED DESCRIPTION OF PREFERRED EMBODIMENTS

Figure 1:
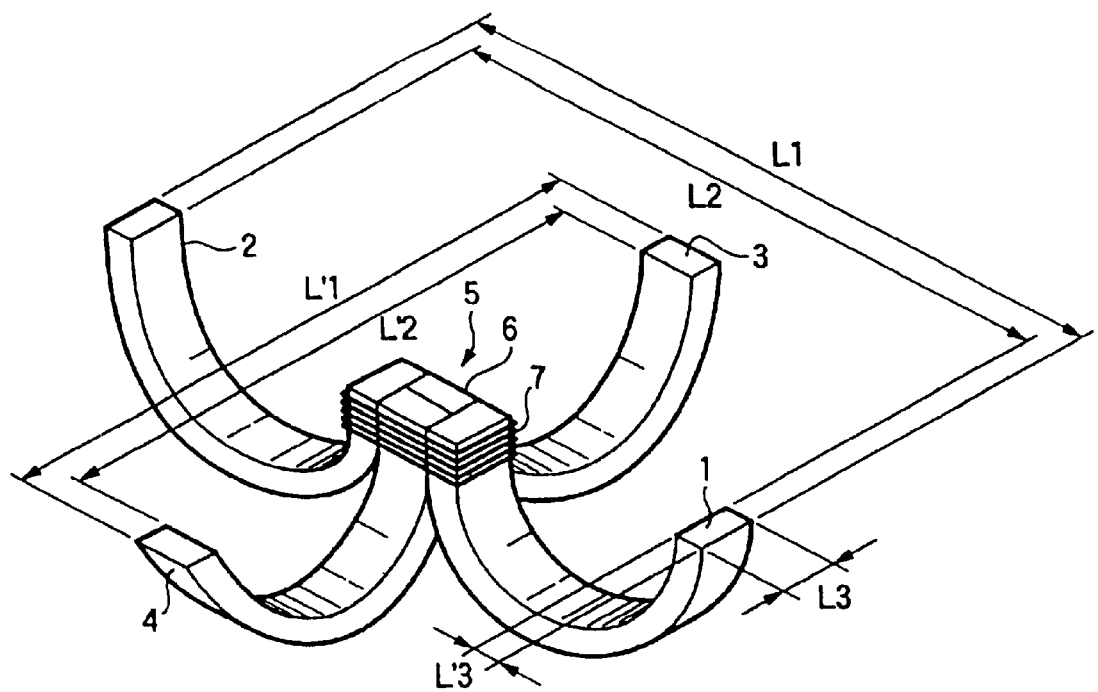
FIG. 1 is a perspective view showing the external appearance of a coil of a coil apparatus according to a first embodiment of the present invention.
Figure 2:
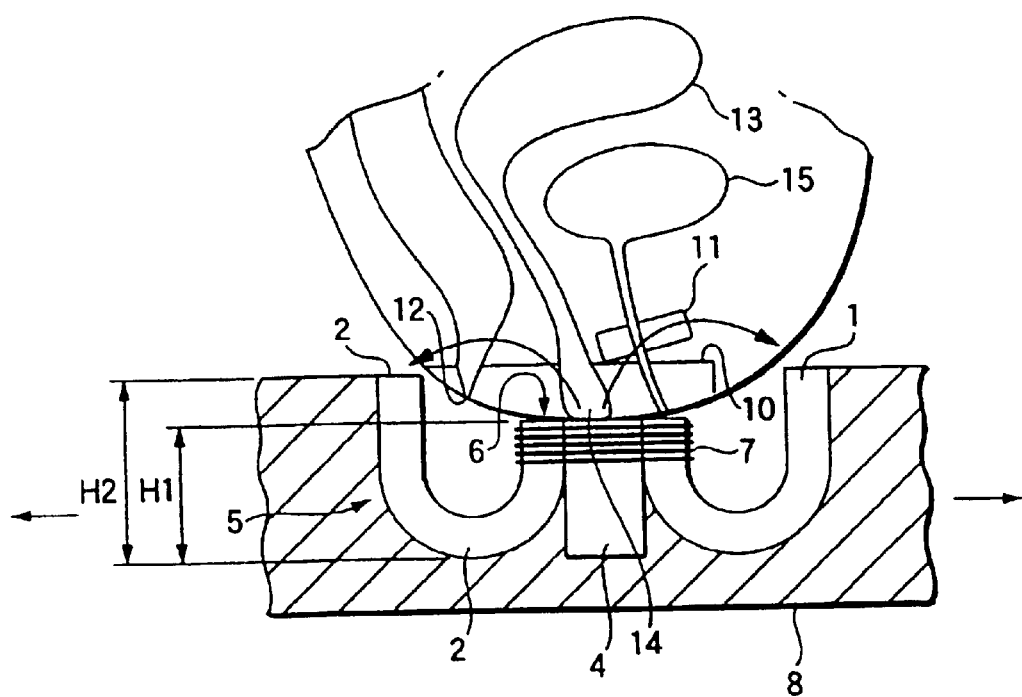
FIG. 2 is a side view of the apparatus depicted in FIG. 1.
Figure 3:
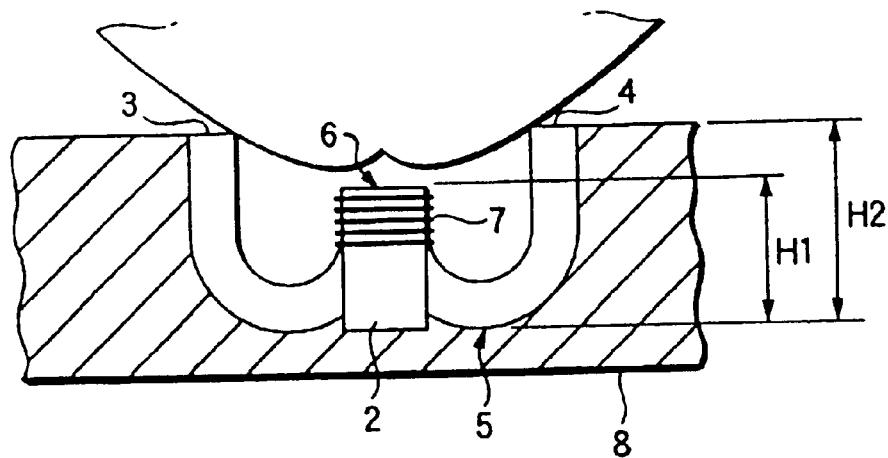
FIG. 3 is a rear view of the apparatus depicted in FIG. 1.

A first embodiment of the present invention will be described below with reference to FIGS. 1, 2 and 3. FIG. 1 is a perspective view showing an important part of a coil apparatus according to this embodiment. FIG. 2 is a side view of the coil apparatus. FIG. 3 is a rear view of the coil apparatus. Incidentally, FIGS. 2 and 3 also show a state in which the coil apparatus is in use practically.

As shown in FIG. 1, the coil apparatus has a core 5. The core 5 is constituted by a J-shaped front core portion 1, a J-shaped rear core portion 2, a U-shaped left core portion 3, and a U-shaped right core portion 4. These core portions have one-side end portions substantially directed in one and the same direction and fixed to one another. In this embodiment, the respective outer surfaces of the one-side end portions of the left and right core portions 3 and 4 are fixed to each other, and the respective outer surfaces of the one-side end portions of the front and rear core portions 1 and 2 are fixed to opposite sides of the portion where the left and right core portions 3 and 4 are fixed to each other. These one-side end portions are fixed to each other to thereby form a center portion 6. The counter-side end portions of the core portions 1 to 4 are arranged at intervals of about 90 degrees from one another with respect to a line of the aforementioned one direction which passes through the center of the center portion 6. A coil 7 is wound on the center portion 6.

As shown in FIGS. 2 and 3, the core 5 is attached to a core support member 8 which is made close to a patient. In this embodiment, the core support member 8 is a chair having a seat plate portion on which the core 5 is attached. As shown in FIG. 2, the respective outer end portions of the front and rear core portions 1 and 2 are configured so as to be longer than the inner end portions thereof. That is, the forward ends of the outer end portions are located at a level higher than the level of the center portion 6. On the other hand, as shown in FIG. 3, the outer end portions of each of the left and right core portions 3 and 4 are made longer than the inner portions thereof. That is, the respective forward ends of the outer end portions of the left and right core portions 3 and 4 are located at a level higher than the level of the center portion 6. When silicon steel laminates are to be used as core materials, it is preferable to use directional silicon steel for efficient stimulation. Because the directional silicon steel has a directional property and magnetic lines of flux are therefore hardly leaked from sides of the core, almost all magnetic lines of flux generated can be concentrated in the center portion 6 so that the vicinity of the anus and portions higher than the anus can be stimulated efficiently.

Incidentally, an electric power supply unit (not shown) is connected to the coil 7 to make the coil 7 generate pulse-like magnetic flux.

In use of the coil apparatus, a patient sits down on the core support member 8 in such a posture as shown in FIGS. 2 and 3 with his or her clothes on. On this occasion, the center portion 6 of the core 5 is positioned substantially in the middle of the purdendal nerve 10 located below the pelvic floor muscle group group 11. Hence, the purdendal nerve 10 is located between the respective outer end portions of the front and rear core portions 1 and 2. The pelvic floor muscle group 11 is located above the purdendal nerve 10 and slightly frontward from the center. The pelvic floor muscle group 11 is, however, in a range which the magnetic flux generated in the front core portion 1 can reach sufficiently. In this embodiment, the patient is a woman. Incidentally, FIG. 2 also shows the arrangement of the anus 12, the uterus 13, the clitoris 14 and the bladder 15.

When the coil 7 is then supplied with a pulse current, pulse-like magnetic flux is generated in the purdendal nerve 10 and the pelvic floor muscle group 11. As a result, an eddy current is induced, whereby the purdendal nerve 10 and the pelvic floor muscle group 11 are stimulated, and urinary incontinence treatment is performed. If the center portion 6 is formed to be low in level as described above, magnetic flux can go deep into the living body, so that the deep regions of the living body can be stimulated.

In the apparatus, the generated magnetic flux density is set to be in a range of from about 0.01 to about 1 tesla and the frequency of the pulse magnetic field is set to be in a range of from 1 to 100 Hz. In the case of medical treatment for stress incontinence, the frequency is preferably set to be in a range of from about tens of Hz to 50 Hz. In the case of medical treatment for urge incontinence, preferably, the frequency is set to be in a range of from about several Hz to 10 Hz.

On the other hand, in FIG. 1, it is preferable that the inner distance defined between the inner side of the outer end of the front core portion and that of the rear core portion, and the inner side of the outer end of the right core portion and that of the left core portion are within 90–230 mmm (L2 and L2' in FIG. 1) and the outer distance defined between the outer side of the outer end of the front core portion and that of the rear core portion, and the outer side of the outer end of the right core portion and that of the left core portion are within 150 to 260 mm (L1 and L1' in FIG. 1). Further, the thickness or width is preferable within 25 to 100 mm (L3 and L3' in FIG. 1). The smaller the sectional area of the center portion 6 is, the more the magnetic flux can be concentrated in the sectional area. However, if the sectional area is too small, the magnetic circuit is saturated. Accordingly, it is preferable to design the sectional area to be the aforementioned value. It is preferable to select the number of turns of the coil 7 wound on the center portion 6 to be in a range of from 6 to 50.

Figure 4:
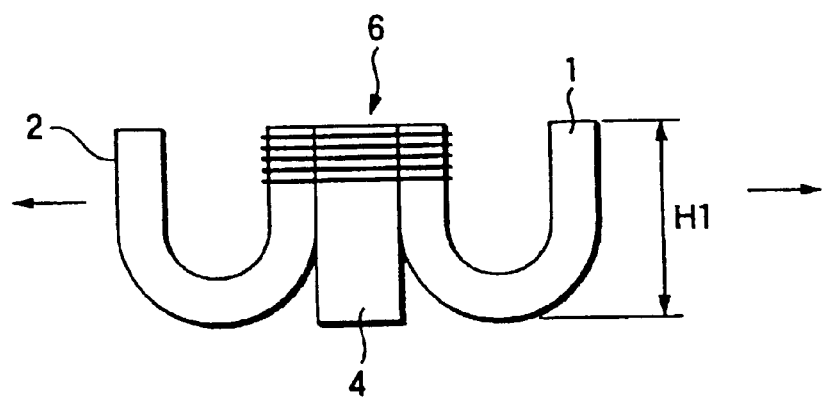
FIG. 4 is a view showing a modified example of the first embodiment.
Figure 5:
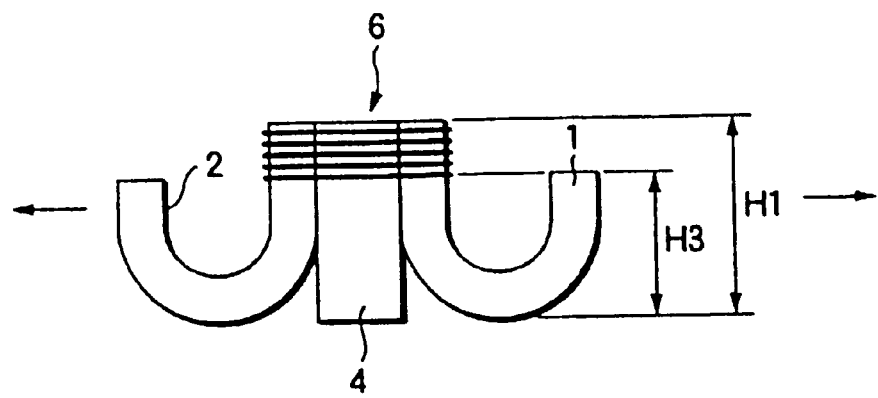
FIG. 5 is a view showing another modified example of the first embodiment.

In this embodiment, the core 5 is configured so that the height H2 of the outer end portion of each of the front and rear core portions 1 and 2 is higher than the height Hi of the center portion 6, and so that the height H2 of the outer end portion of each of the left and right core portions 3 and 4 is higher than the height Hi of the center portion 6. Alternatively, as shown in FIG. 4, the core 5 may be configured so that the height of the outer end portion of each of the core portions 1 to 4 is equal to the height Hi of the center portion 6. Alternatively, as shown in FIG. 5, the core 5 may be configured so that the height H3 of the outer end portion of each of the front and rear core portions 1 and 2 is lower than the height Hi of the center portion 6, and is lower than the height H1 of the outer end portion of each of the left and right core portions 3 and 4. When an optimally shaped core is used as the core 5 in accordance with the size of the patient and the region to be stimulated, medical treatment can be made efficiently.

Although this embodiment has shown the case where the coil 7 is wound on the center portion 6, the present invention does not limit the wound portion to the center portion 6, but may be applied to a case where the coil 7 is wound on portions of the core portions 1 to 4 other than the center portion 6.

Incidentally, a single wire (electric wire), a hollow copper pipe or a Litz wire may be used as a material of the coil. If the current applied to the coil is small, safety is retained because the amount of heat generated in the coil is small even in the case where a single wire is used. However, if the coil current is intensified to increase the intensity of stimulation, the patient faces a risk of a burn because of a large amount of heat generated. Therefore, a method of circulating a coolant in a coil of a copper pipe is used heretofore. As a further measure for reducing the amount of heat generated in the coil, a coil made of a Litz wire may be used. This measure is effective in improving electric current properties when the frequency of the coil current is high. As a result, AC resistance is reduced, so that loss is reduced and the amount of heat generated is reduced.

Figure 6:
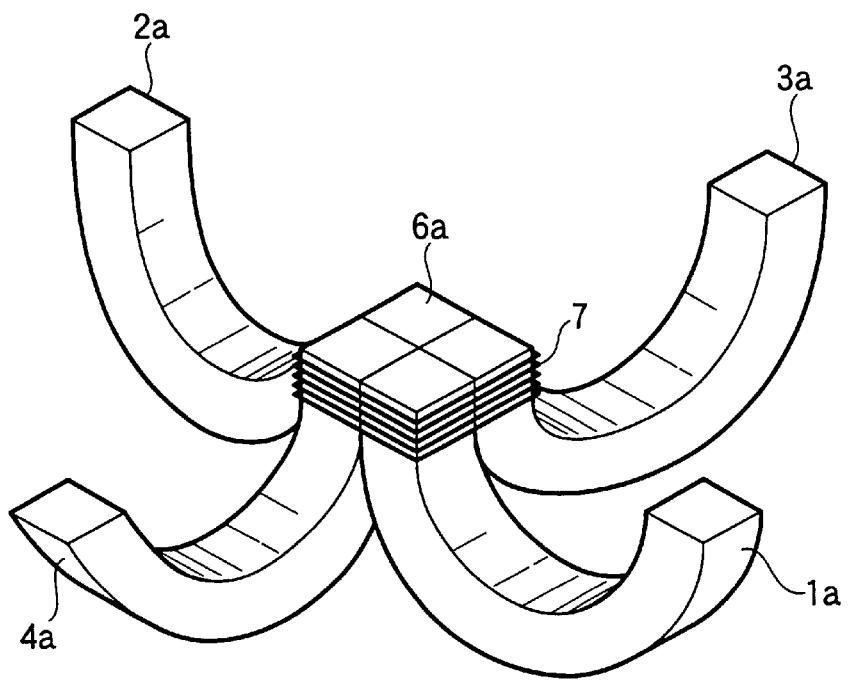
FIG. 6 is a view showing a further modified example of the first embodiment.

Although this embodiment has shown the case where the section of each of the core portions 1 to 4 constituting the core 5 is a rectangle, the present invention may be applied also to the case where the section of each of front, rear, left and right core portions 1a, 2a, 3a and 4a is a square as shown in FIG. 6. In this case, the center portion 6a can be shaped like a square, so that magnetic flux can be uniformly distributed, applying the stimulation equally and efficiently to the pelvic floor muscle group or the pudendal nerve.

In this embodiment, each of the core portions may be made of laminates of silicon steel, directional silicon steel or Permalloy, Sendust or permendur. Alternatively, each of the core portions may be integrally molded from a powder magnetic core such as ferrite, or the like. The fixation of these core portions may be performed by screws or by any other means.

Figure 7:
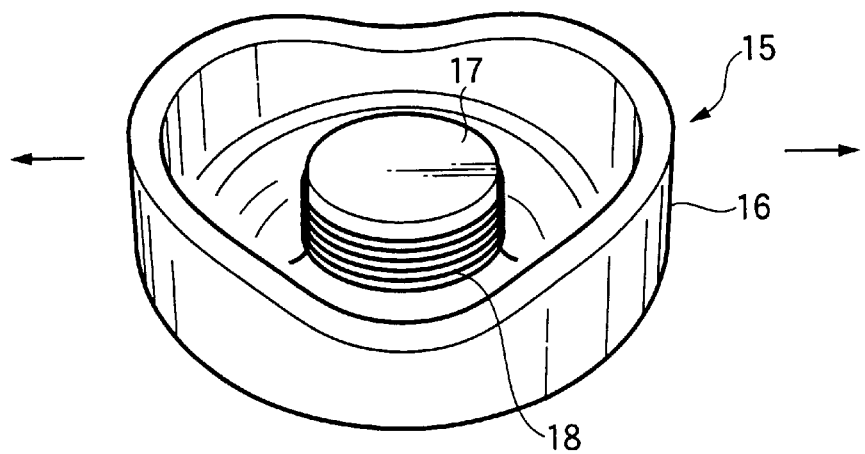
FIG. 7 is a perspective view showing the external appearance of a coil of a coil apparatus according to a second embodiment of the present invention.
Figure 8:
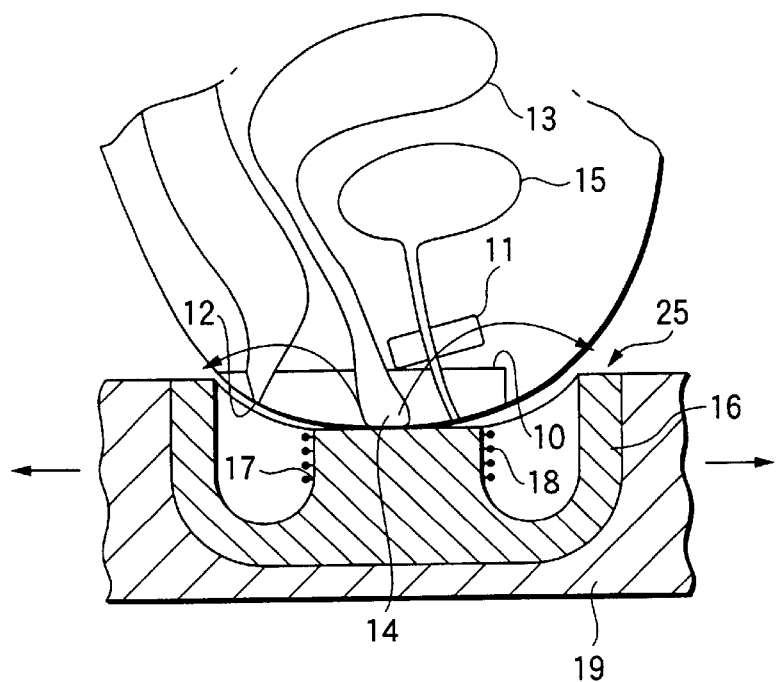
FIG. 8 is a side sectional view of the apparatus depicted in FIG. 7.

Although this embodiment has shown the case where four core portions as core elements are fixed to one another to thereby form a core, the present invention may be applied also to a case where a core having the same contour as that of the aforementioned core is integrally molded. For example, a powder magnetic core such as ferrite, or the like, may be used. Further, although this embodiment has shown the case where the number of core portions is four, the number of core portions may be five or more A second embodiment of the present invention will be described below. FIG. 7 is a perspective view showing the external appearance of the coil apparatus. FIG. 8 is a sectional view of the coil apparatus. As shown in FIGS. 7 and 8, the coil apparatus has a core 25 constituted by a bowl-shaped base portion 16, and a protrudent portion 17 protruded from the inner center of the base portion 16. The bowl-shaped base portion 16 has an edge portion shaped like waves having two higher portions opposite to each other and two lower portions opposite to each other. These higher and lower portions are arranged at intervals of about 90 degrees with respect to the protrudent portion 17.

A coil 18 is wound on the protrudent portion 17. The core 25 is attached to a core support member 19. Also in this embodiment, the core support member 19 is provided as a chair in the same manner as that in the first embodiment. That is, the core 25 is mounted on the seat base portion of the chair. Further, an electric power supply unit not shown is connected to the coil 18.

In use of the coil apparatus, a patient sits down on the core support member 19 in such a posture as shown in FIG. 8 with his or her clothes on. On this occasion, the protrudent portion 17 of the core 25 is positioned substantially in the middle of the purdendal nerve 10 which is located below the pelvic floor muscle group 11. Hence, the purdendal nerve 10 is fitted in the inside of and above the base portion 16. The pelvic floor muscle group 11 is located slightly frontward from the center of the purdendal nerve 10. The pelvic floor muscle group 11 is, however, in a range which magnetic force of the core 25 can reach sufficiently. Also in this embodiment, the patient is a woman. Incidentally, the positions of other organs are as shown in FIG. 2.

When the coil 18 is then supplied with a pulse current, pulse-like magnetic flux is generated in the purdendal nerve 10 and the pelvic floor muscle group 11. As a result, an eddy current is induced. Thus, the purdendal nerve 10 and the pelvic floor muscle group 11 are stimulated, so that urinary incontinence treatment is performed.

In this embodiment, it is preferable that the protrudent portion 17 has a diameter of about 30–80 mm, and the base portion 16 has an inner diameter of about 90–230 mm and an outer diameter of about 150–260 mm. Further, preferably, the coil 18 is configured such that the number of turns of the coil, the material and structure of the coil, and the density and frequency of magnetic flux generated from the coil, are set to have the same values as those in the first embodiment.

In this embodiment, the core 25 may be made of laminates of silicon steel, directional silicon steel or Permalloy, Sendust or permendur. Alternatively, the core 25 may be molded from a powder magnetic core such as ferrite, or the like.

Figure 9:
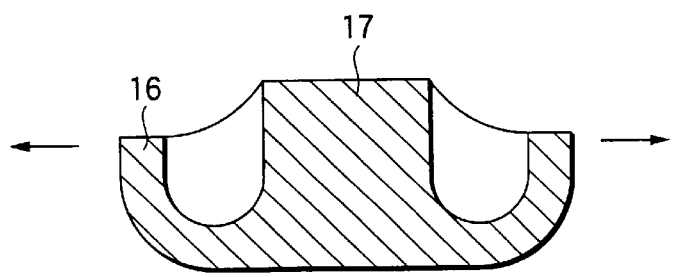
FIG. 9 is a view showing a modified example of the second embodiment.
Figure 10:
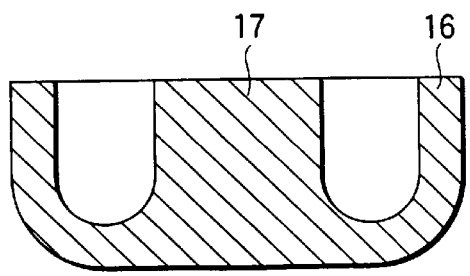
FIG. 10 is a view showing another modified example of the second embodiment.

This embodiment has shown the case where the core 25 is configured so that the front and rear edge portions of the base portion 16 are high, and so that the left and right edge portions of the base portion 16 and the protrudent portion 17 are low. Alternatively, as shown in FIG. 9, the core 25 may be configured so that the front and rear edge portions of the base portion 16 are low, and so that the left and right edge portions of the base portion 16 and the protrudent portion 17 are high. Alternatively, as shown in FIG. 10, the core 25 may be configured so that the whole of the edge portion of the base portion 16 is equal in height to the protrudent portion 17. If a core optimally shaped in accordance with the size of the patient and the region to be stimulated is used as the core 25, medical treatment can be made efficiently.

Figure 11:
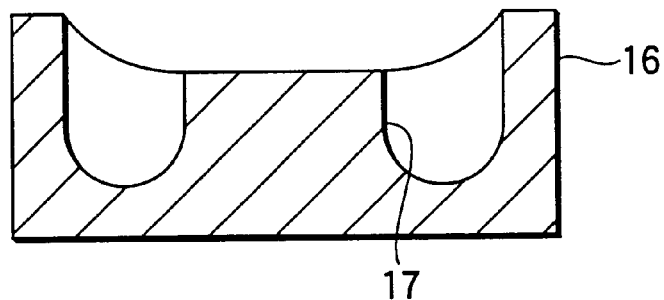
FIG. 11 is a view showing a further modified example of the second embodiment.
Figure 12:
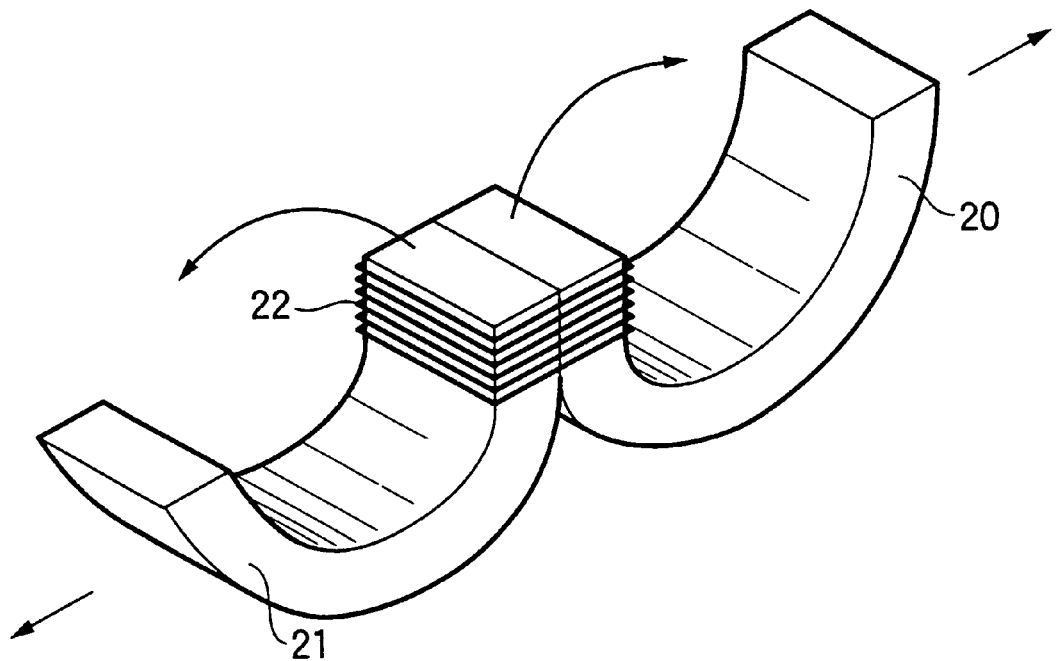
FIG. 12 is a perspective view showing the external appearance of a coil of a coil apparatus according to the background art.
Figure 13A:
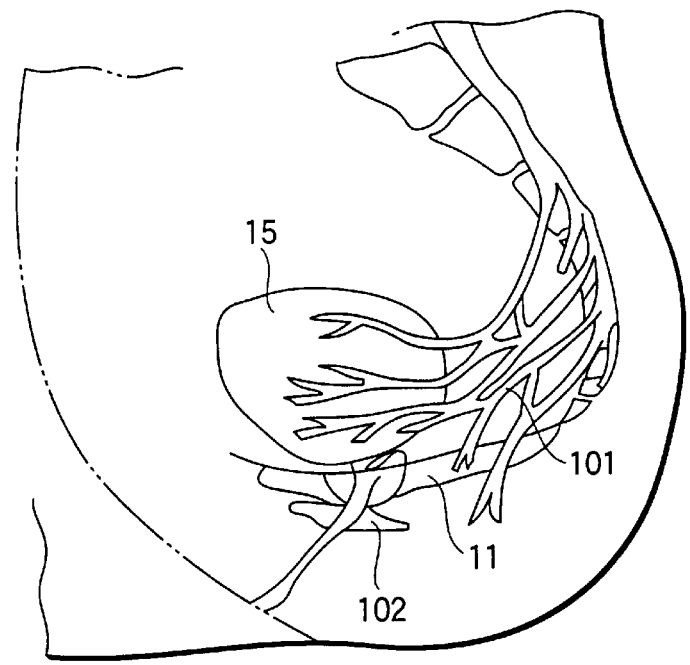
FIGS. 13(a) and (b) are anatomy views of human body.
Figure 13B:
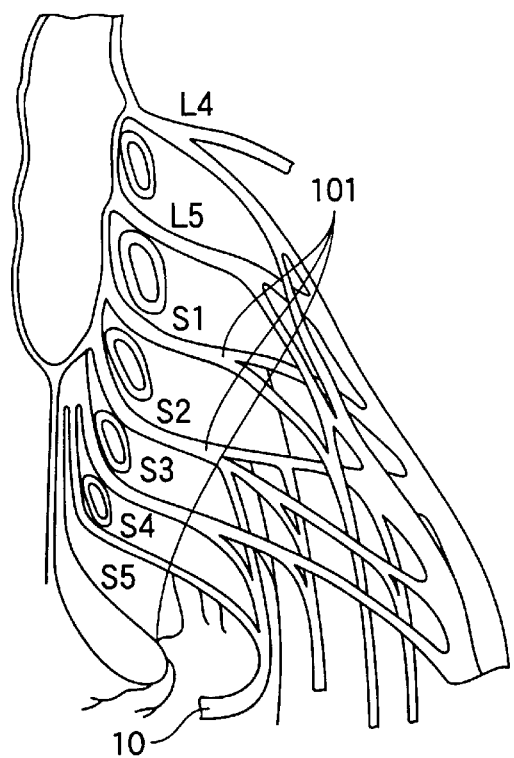

Although this embodiment has shown the case where the base portion 16 is shaped like a bowl, the present invention may be applied also to the case where the base portion 16 is shaped like a closed-end tube, as shown in FIG. 11.

The aforementioned respective embodiments have shown the case where the core support member is provided as a chair. Alternatively, any core support member such as a bed, a stand, or the like, may be used so long as it can be attached close or near to the patient. For example, the core support member may be provided as a cushion or as underwear.

According to the present invention, the region necessary to be stimulated can be entirely stimulated and magnetic flux can be concentrated in the region to be stimulated so that the magnetic flux does not reach the other organs. Hence, electric power consumption can be reduced. Moreover, regions not to be stimulated can be reduced in stimulation so that safety in medical treatment can be improved.

According to the present invention, magnetic flux generated from the core applied for a patient to at least forward to behind direction of the pelvic floor muscle group and right to left direction where the second to fourth sacral nerves innervated in said right to left direction or the purdendal nerve branched from the second to fourth sacral nerves.

According to the present invention, all the region to be stimulated can be stimulated uniformly in addition to the effect similar to that obtained in the present invention describe above.

What is claimed is:

1. A coil apparatus for urinary incontinence treatment, said coil apparatus comprising:
    a core with at least four core elements, each of said core elements being U-or J-shaped, each of said core elements having one side end portion and another side end portion opposite to said one side end portion, respectively, said one side end portions being directed substantially in one and the same direction, said one side end portions being fixed to one another at a portion which is defined as a center portion of said core, said other side end portions being extended in different directions, respectively, from said center portion so that said other side end portions are disposed at equal intervals from one another when said center portion is viewed as a center point;
    a coil wound on said core; and
    a core support member to which said core is attached, said core support member being able to be disposed close or near to a patient.

2. A coil apparatus for urinary incontinence treatment comprising:
    a core integrally formed by a mold, said core having at least four core elements, each of said core elements being U- or J-shaped, said core elements having one side end portion and another side end portion opposite to said one side end portion, respectively, said one side end portions being directed substantially in one and the same direction, said one-side end portions being fixed to one another at a portion which is defined as a center portion of said core, said the other side end portions each being extended in a separate direction respectively from said center portion so that said other side end portions are disposed at equal intervals from one another when said center portion is viewed as a center point;
    a coil wound on said core; and
    a core support member to which said core is attached, said core support member being able to be disposed close or near to a patient.

3. A coil apparatus for urinary incontinence treatment comprising:
    a core having at least four core elements for generating magnetic flux;
    a core support member to which said core is attached;
    wherein said core generates the magnetic flux to a patient in forward and rear directions of a pelvic floor muscle group and in right and left directions along second to fourth sacral nerves innervated in said right and left directions serving as a trunk branching to a purdendal nerve.

* * * * *